United States Patent [19]

Pohndorf

[11] 4,422,460
[45] Dec. 27, 1983

[54] POSITIONABLE LOCATING AND ORIENTING WING FOR A PACING LEAD

[75] Inventor: Peter J. Pohndorf, Miami Shores, Fla.

[73] Assignee: Cordis Corporation, Miami, Fla.

[21] Appl. No.: 366,816

[22] Filed: Apr. 8, 1982

[51] Int. Cl.³ .............................................. A61N 1/04
[52] U.S. Cl. ................... 128/786; 128/419 P
[58] Field of Search .................... 128/784–786, 128/419 P, 214 R, 214.4, 642, 348, 349 R, 772, DIG. 9; 604/164–167, 281

[56] References Cited

U.S. PATENT DOCUMENTS

| | | | |
|---|---|---|---|
| 3,589,361 | 6/1971 | Loper et al. | 128/214.4 |
| 3,783,876 | 1/1974 | Dye | 128/348 X |
| 3,809,081 | 5/1974 | Loveless | 128/214.4 |
| 3,817,251 | 6/1974 | Hesson | 128/348 |
| 3,860,006 | 1/1975 | Patel | 128/214.4 X |
| 4,166,469 | 9/1979 | Littleford | 128/784 |
| 4,177,809 | 12/1979 | Moorehead | 128/214.4 |
| 4,192,305 | 3/1980 | Seberg | 128/214.4 |
| 4,300,553 | 11/1981 | Seberg | 128/214.4 |
| 4,357,947 | 11/1982 | Littleford | 128/419 P X |

FOREIGN PATENT DOCUMENTS

| | | | |
|---|---|---|---|
| 67214 | 6/1949 | German Democratic Rep. | 128/348 |
| 6715573 | 5/1968 | Netherlands | 128/214.4 |

OTHER PUBLICATIONS

Littleford et al., "A New Temp. Atrial Pacing Catheter . . . ", PACE, vol. 4, Jul.-Aug. 1981, pp. 458-464.

*Primary Examiner*—Lee S. Cohen
*Attorney, Agent, or Firm*—Henry W. Collins; Thomas R. Vigil

[57] ABSTRACT

The pacing lead assembly (10) comprises a flexible pacing lead (12) having, at the proximal end thereof, terminals (14, 16) for connecting the lead (12) to a pulse generator, and having a flexible bent or curved configuration (23) in an outer end portion (22) thereof with an electrode assembly (24) including an electrode (28) at the distal end (25) of the pacing lead (12). A positionable, locating, orienting and stabilizing device (34) has a passageway (38) therethrough and is received over the lead (12) such that the device (34) can be rotated on the pacing lead (12). A cooperating locking hub (36) is fixed on the lead (12) and adapted to mate and lock with the device (34) in a predetermined position of the device (34) whereby the device (34), when locked in place in the predetermined position, has a predetermined orientation relative to the bent or curved configuration (23) in the outer end portion (22) of the pacing lead (12) and whereby the device (34) in its unlocked position can be rotated to an unobtrusive position relative to the outer end portion (22) of the pacing lead (12).

11 Claims, 4 Drawing Figures

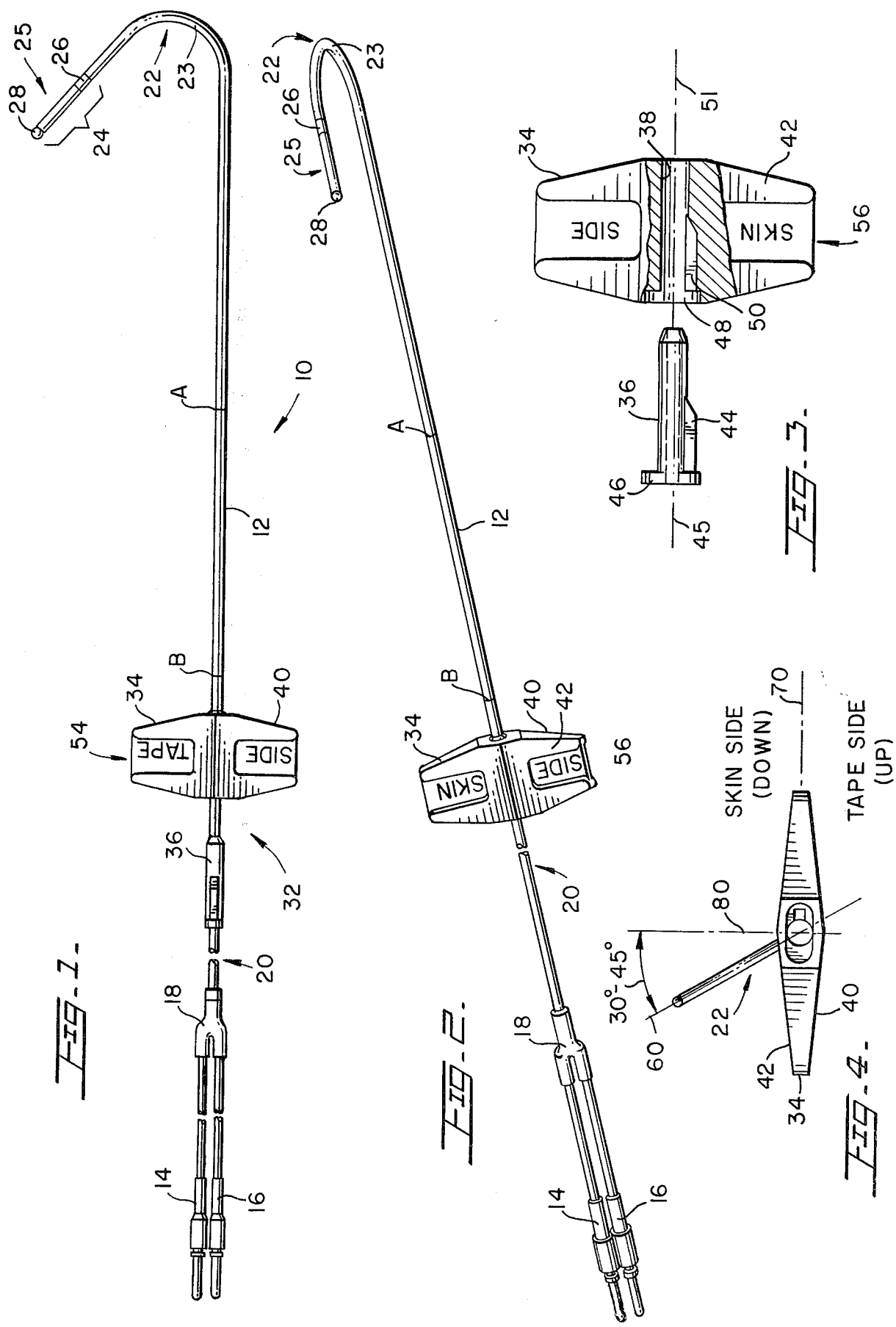

POSITIONABLE LOCATING AND ORIENTING WING FOR A PACING LEAD

TECHNICAL FIELD

The present invention relates to a "pacemaker" system and more particularly to an improvement in a pacing lead assembly thereof. More specifically, the invention is directed to a positionable locating wing that is mounted on the pacing lead of the assembly and which can be rotated on the lead prior to use of the pacing lead assembly and then locked in a predetermined locating position on the pacing lead when the pacing lead assembly is ready for use, i.e., is ready for insertion of the distal end of the lead into a heart.

BACKGROUND ART

Heretofore hearts have been effectively "paced" by electrical pulses applied to the heart, namely to the endocardial wall within the right atrium. However, difficulties have been encountered in locating the extremity of an electrode at the end of a pacing lead in an appropriate location within the right atrium and in a stable manner, even with the benefit of fluoroscopy. In fact, without the benefit of fluoroscopy, it has heretofore been impossible properly to insert a temporary pacing lead with an electrode at the end thereof into the right atrium of a heart.

In view of this inability to effectively locate an electrode at the end of a pacing lead assembly within the right atrium in a stable manner, most pacing electrodes at the end of a pacing lead assembly are inserted into the right ventricle wherein stable positioning of the electrode can be obtained. In this procedure, however, it has been found to be difficult to manipulate a pacing electrode through the tricuspid valve and into the right ventricle without fluoroscopy.

Recently, and as disclosed in U.S. Pat. No. 4,166,469 issued Sept. 4, 1979, there is disclosed an apparatus and a related method for effecting a rapid and generally atraumatic insertion of a pacemaker electrode through the subclavian vein, through the superior vena cava and into the right atrium. The apparatus disclosed utilizes a "J" shaped electrode which it has been found, can be inserted through the right subclavian vein into the right atrium and when the electrode is oriented and manipulated in a predetermined direction and manner, the tip of the electrode will always engage the right atrium in a stable manner.

Also it has been recognized that an electrode having an appropriately oriented bend at the distal end thereof will pass through the tricuspid valve into the right ventricle when it is inserted in a predetermined manner and direction through the right subclavian vein.

It has also heretofore been proposed to provide a wing for orienting and stabilizing the position of the electrode, such orienting and stabilizing wing being mounted on the sheath of the lead connected between the electrode at the distal end of the pacing lead assembly and a terminal member at the proximal end of the pacing lead assembly. Such orienting and stabilizing wing indicates the orientation of the curve or bend situated in the outer end of the pacing lead after the distal end of the pacing lead has been inserted into the heart and can be taped to the patient's skin to stabilize the electrode after electrical contact has been properly established between the tip of the electrode and the heart.

The orienting and stabilizing wing is fixed on the sheath of the pacing lead at a position outside the patient's body when the distal end of the pacing lead has been inserted into the heart. The wing includes left and right wing portions which extend laterally on either side of and from the sheath. The lateral direction of the pair of wing portions, i.e., the plane of the wing, indicates the orientation of the curve or bend in the outer end portion of the pacing lead and indicia are provided on the wing for indicating which side of the wing should be facing away from the patient and which side should be facing the patient's skin. The desired orientation is such that when the plane of the wing is flat against the patient's skin, with the "tape side up" indicia facing upwardly, the J shaped flexible outer end portion of the pacing lead with an electrode at the tip of the distal end thereof, in the case of an atrial electrode, lies in a plane which is transverse to the plane of the wing and at an angle of approximately 90° to the plane of the wing.

Further it has heretofore been proposed in U.S. Pat. No. 4,300,553 to provide a catheter placement assembly with a wing.

The winged assemblies described above each have a three dimensional configuration.

As will be described in detail hereinafter in connection with the description of the present invention, it is desirable that, for packaging, storage and shipping purposes, the pacing lead assembly have a more planar or flat configuration for being placed flush against a packaging substrate. Accordingly, the pacing lead assembly of the present invention differs from the pacing lead assemblies with fixed wings described above by providing a positionable locating wing which is rotatable on the sheath of the lead of the pacing assembly so that it can be rotated to a flat position for packaging of the pacing lead assembly and then, prior to use, be locked in an orienting and locating position on the sheath such that the plane of the curved end portion of the pacing lead has a predetermined orientation to the plane of the wing as will be described in greater detail hereinafter.

SUMMARY OF THE INVENTION

According to the invention there is provided in a pacing lead assembly comprising a flexible lead including at least one insulated conductor having a proximal end and a distal end, means at the proximal end for electrically connecting the insulated conductor to a pulse generator, a flexible bent or curved configuration in an outer end portion of the lead adjacent the distal end of the lead and an electrode assembly including at least one electrode mounted at the distal end of the pacing lead, the at least one electrode being connected to the conductor, the improvement comprising a positionable, locating, orienting and stabilizing device mounted on the pacing lead and having a passageway through which the pacing lead is received such that said device can be rotated in the pacing lead and cooperating locking means fixed on the lead and adapted to mate and lock with said device in a predetermined position of said device, whereby said device when locked in place in said predetermined position on the lead, has a predetermined orientation relative to the bent or curved configuration in the outer end portion of the pacing lead and whereby said device in its unlocked position can be rotated to a non-obtrusive position relative to the outer end portion of the pacing lead, said device being generally flat and planar in shape and said unobtrusive position being a position where the plane of said flat planar device is generally coplanar with the plane of the bent or curved configuration on the outer end portion of the pacing lead, whereby the pacing lead assembly can be packaged in a flat or flush position on a substrate.

BRIEF DESCRIPTION OF THE DRAWINGS

FIG. 1 is a plan view of the pacing lead assembly of the present invention with a positionable locating wing thereof rotated on the pacing lead so as to lie in the same plane in which a curved J shaped outer end portion of the lead lies.

FIG. 2 is a perspective view of the pacing lead assembly shown in FIG. 1 after the locating wing has been rotated to a desired orienting position and slid on the sheath into engagement with a locking key for locking the wing in a desired orientation relative to the J shaped end portion.

FIG. 3 is an enlarged plan view of a hub on which the locking key is situated and the locating wing with portions broken away to show the interior configuration thereof adapted to mate with the locking key.

FIG. 4 is a sectional view of the pacing lead taken along line 4—4 of FIG. 2 and shows the orientation of the outer end portion of the lead relative to the locked position of the locating wing.

BEST MODE FOR CARRYING OUT THE INVENTION

Referring now to FIG. 1 there is illustrated therein a temporary pervenous J-atrial pacing lead assembly 10 constructed in accordance with the teachings of the present invention.

The pacing lead assembly 10 includes a pacing lead 12 which, as is well known in the art, has an outer insulative sheath and one or two insulated flexible wire conductors within the sheath. The wire conductors (not shown) extend the length of the pacing lead 12 from lead terminals 14 and 16, that are coupled by means of a coupling 18 to the proximal end 20 of the lead 12, to an outer end portion 22 of the lead 12. The end portion 22 has a curved section 23 and an electrode assembly 24 at distal end 25 of the lead 12. The electrode assembly 24 includes an anode electrode 26 in the form of a band at the end of the curved section 23 and a semi-spherical cathode electrode 28 at the tip or end of the electrode assembly 24. The band electrode 26, of course, is spaced from and insulated from the tip electrode 28.

As shown, the outer end portion 22 has a curved segment 30 which forms the outer end 22, including the electrode assembly 24, with a "J" shape.

In accordance with the teachings of the present invention, the pacing lead assembly 10 includes a locating, orienting and stabilizing assembly 32 which includes a flat, planar shaped device 34 or wing 34 (having right and left laterally extending wing portions) and a locking hub 36. The wing 34 has a passageway 38 (FIG. 3) therethrough which has a larger diameter than the outer diameter of the lead 12. As shown, the wing 34 is received over the lead 12 and, in the position thereof shown in FIG. 1, can be rotated about the axis of the lead 12. In this way, and as will be described in greater detail hereinafter, the plane of the wing 34 can be aligned with the plane containing the J shaped outer end portion 22 of the pacing lead 12.

The wing 34 has a tape side 40 and a skin side 42. In use, when the wing 34 is moved into mating and locking engagement with the locking hub 36 the skin side 42, which is adapted to lie against the patient's skin, is locked to the hub 36 with a predetermined orientation relative to the J shaped outer end portion 22. The tape side 42 will face upwardly and is adapted to receive tape thereover for temporarily affixing the wing 34 to the patient's skin.

As best shown in FIGS. 1 and 3, the locking hub 36 has an outer diameter approximately equal to the diameter of the passageway 38 and has a rib 44 which extends radially outwardly from the axis 45 of the hub 36 and longitudinally parallel to the axis of the hub 36 from an end flange 46 to form a locking key 44.

As shown in FIG. 3, the passageway 38 through the wing 34 is configured at one end to have a countersunk cavity 48 and a longitudinal slot 50 extending radially and longitudinally of the axis 51 of the passageway 38 such that the slot 50 will mate with the rib 44 and the countersunk cavity 48 will mate with the end flange 46 when the wing 34 is properly oriented relative to the hub 36 as shown in FIG. 3 and the wing 34 is moved over the hub 36 (to the right, viewing same as shown in FIGS. 1 and 3) to lock the wing 34 against rotation relative to the hub 36 fixed on the pacing lead 12.

As shown in FIGS. 1 and 4, the side 40 of the wing 34 has indicia 54 thereon indicating that that side should face upwardly from the patient's skin for receiving tape thereon when the wing 34 is locked in place on the hub 36. This indicia 54 can take the form of words such as "Tape Side" or "Up".

Likewise, the side 42 has indicia 56 thereon to indicate that this side should be placed against the skin and this indicia 56 can take the form of the words "Skin Side" or "Down".

Preferably, the indicia 54 on the side 40 of the wing 34 are in the form of a trademark of the manufacturer of the pacing lead assembly 10 and the indicia 56 of the other side 42 being the words "Skin Side".

Also, preferably, the hub 36 is located approximately 30 cm from the distal end 25 of the pacing lead 12. Also, there are provided depth indicating bands A and B at predetermined locations along the length of the lead 12. The band A indicates a penetration depth of 10 cm of the pacing lead 12 and band B indicates a penetration depth of 20 cm of the pacing lead 12.

The hub 36 and the flat, planar device or wing 34 are made of a body compatible plastic material such as polyurethane.

The pacing lead assembly 10 with the flat planar device or wing 34 positioned so as to be coplanar with the plane containing the J shaped end portion 22 is received flat or flush on a packaging substrate (not shown) where a layer of clear plastic can be heat sealed to the substrate around the assembly 10 to form a blister pack. The substrate can be relatively stiff, i.e., a piece of cardboard with a layer of flexible clear plastic thereover to form a generally flat package with the side 40 of the wing 34 facing upwardly with the manufacturer's trademark showing through the clear plastic.

In use, a doctor or medical assistant will remove the blister covering from the packaging for the pacing lead assembly 10 and remove the assembly 10 from the package. Of course, before inserting the electrode assembly 24 at the outer end 22 of the pacing lead 12 into a patient, the patient is properly prepared and normal sterilization procedures are observed.

Initially a puncture is made through the patient's skin in the area adjacent the clavicle by inserting a small thin-walled 18 gauge needle into the right subclavian vein. Thereafter, a removable introducer is inserted into the vein in the manner described in U.S. Pat. No. 4,166,469.

Once the introducer sleeve is properly inserted the curved section 23 in the outer end portion 22 of the pacing lead 12 is straightened. The electrode assembly 24 is then inserted through the removable introducer sleeve into the right subclavian vein.

Once the straightened distal end 25 containing the electrode assembly 24 has been inserted down the introducer sleeve and into the right subclavian vein, the pacing lead 12 is manipulated to move the distal end 25 through the superior vena cava and into the right atrium. The removable introducer sleeve is then removed by peeling it away to allow the wing 34 and hub 36 to be positioned close to the entrance site into the subclavian vein. At this point in the technique, the electrode assembly 24 has been inserted as desired so that the straightened end portion 22 is positioned in the right atrium with the wing 34 disposed exteriorly of the patient's skin.

If a stylet had been used to maintain the curved section 23 straight during the insertion of the outer end portion 22 into the right subclavian vein, the superior vana cava and then into the right atrium, the stylet is now removed so that the curved section 23 can flex back to its curved configuration as shown in FIGS. 1, 2 and 4. In either event, the curved section 30 resumes its normal curved configuration as shown in FIGS. 1, 2 and 4.

Assuming the physician has inserted the electrode assembly 24 a sufficient distance into the right subclavian vein, down the superior vena cava and into the right atrium as determined by the depth indicating bands A and B, then the wing 34 is locked to the hub 36 and positioned flush against the patient's skin. The curved section 23 then will assume a direction in which the electrode assembly 24 and particularly the cathode 28 thereof is pointed directly upwardly toward the right atrial appendage.

This is because of the unique relationship of the curvature from the right subclavian vein running down to and through the superior vena cava and into the right atrium.

For the cathode electrode 28 of the electrode assembly 24 to be in the right position for supplying pacing electrical pulses to the right atrium, the plane of the outer end portion 22 containing the curved section 23 should lie in a plane 60 which is transverse to a plane 70 of the wing 34 and such that the planes intersect each other at an angle of from 45° to 60° C. This orientation is shown in FIG. 4 where the angle of the plane 60 containing the J shaped outer end portion 22 is 30° to 45° from a plane 80 normal to the plane 70 of the wing 34.

As a result, the wing 34, when locked on the locking hub 36 and placed flush against a patient's skin, locates or orients the curved outer end portion 22 of the pacing lead 12 such that the electrode assembly 24 is pointed in a desired manner and direction in the pocket in the right atrial appendage in the right atrium. Once so located, the attending physician can then connect the terminal leads 14 and 16 to a pacemaker pulse generator and then pull the pacing lead 12 slightly outward from the puncture wound in the skin and away from the subclavian vein a distance of between 1 and 7 cm as determined by the depth indicating bands A and B to ensure that the conductive cathode electrode 28 engages the surface underneath the right atrial appendage 26.

Next, the physician will ascertain appropriate electrode "capture" by reference to the pulse generator.

Because of the spherical configuration of the cathode electrode 28 that electrode makes a broad electrical contact with the wall of the right atrium in the pocket of the appendage without damage to the wall. Also, the cathode electrode 28 stays in place because of the tension in the flexible curved section 23 despite continual movement of the atrial wall.

Also it will be understood that the manipulation of the pacing lead assembly 10 to properly position the cathode electrode 28 can take place without the benefit of fluoroscopy thus permitting a temporary pervenous J-atrial pacing lead assembly 12 and particularly the electrode 28 at the end thereof to be placed easily and quickly into the right atrium for the purpose of pacing the atrium under emergency or temporary conditions. Once the electrode assembly 24 has been inserted and the electrode 28 has been located in the desired position within the atrium, the electrode assembly 24 may then be stabilized. This is accomplished by placing the wing 34 flat or flush against the patient's skin near the puncture wound and then fastening the wing 34 against the patient's skin by a strip of tape. During atrial pacing, the curved section 23 and the distal end 25 will be subject to significant movement and thus torque. However, the electrode assembly 24 will be, and is, stabilized against losing its position because of the taping of the locating, orienting and stabilizing wing 34 to the patient's skin.

Although the locating, orienting and stabilizing assembly 32 has been described with reference to its use with a J-atrial pacing lead assembly, it is to be understood that the locating, orienting and stabilizing assembly 32 can be utilized in a ventricular electrode pacing lead assembly.

It will be appreciated from the foregoing description that the locating, orienting and stabilizing assembly 32 of the pacing lead assembly 10 of the present invention has a number of advantages, some of which have been described above and others of which are inherent in the invention. In particular, the positionable wing 34 of the locating, orienting and stabilizing assembly 32 permits the pacing lead assembly 10 to be mounted flat or flush with a substrate in a blister pack and later, upon removal from the package, the wing 34 can be rotated to a locating and orienting position and moved into locking engagement with the hub 36 whereby the wing 34 can be utilized for locating, orienting and stabilizing the electrode assembly 24 at the distal end 25 of the pacing lead 12 when it is inserted into the right atrium of a patient's heart.

Also it will be apparent to those in the art that modifications can be made to the pacing lead assembly 10, and more particularly to the locating, orienting and stabilizing assembly 32 thereof, without departing from the teachings of the present invention. Accordingly, the scope of the invention is only to be limited as necessitated by the accompanying claims.

I claim:

1. In a pacing lead assembly comprising a flexible pacing lead including at least one insulated conductor having a proximal end and a distal end, means at the proximal end for electrically connecting the insulated conductor to a pulse generator, a flexible bent or curved configuration in an outer end portion of the lead adjacent the distal end of the lead and an electrode assembly including at least one electrode mounted at the distal end of the pacing lead, the at least one electrode being connected to the conductor, the improvement comprising a positionable, locating, orienting and stabilizing device mounted on the pacing lead and having a passageway through which the pacing lead is received such that said device can be rotated on the pacing lead and cooperating locking means fixed on the lead and adapted to mate and lock with said device in a predetermined position of said device, whereby said device when locked in place in said predetermined position on the lead, has a predetermined orientation relative to the bent or curved configuration in the outer end portion of the pacing lead and whereby said device in its unlocked position can be rotated to a non-obtrusive position relative to the outer end portion of the pacing lead, said device being generally flat and planar in shape and said unobtrusive position being a position where the plane of said flat planar device is generally coplanar with the plane of the bent or curved configuration in the outer end portion of the pacing lead, whereby the pacing lead assembly can be packaged in a flat or flush position on a substrate.

2. The pacing lead assembly of claim 1 wherein said predetermined orientation is where the plane of the bent or curved configuration in the outer end portion of the pacing lead is transverse to the plane of said flat, planar device.

3. The pacing lead assembly of claim 2 wherein the angle between said planes is between 45° and 90°.

4. The pacing lead assembly of claim 1 wherein said outer end portion has a curve therein so as to provide the outer end with a J shape and said predetermined orientation of the plane containing the J shaped outer end portion relative to the plane of said flat planar device is where the planes intersect each other at an acute angle of between 45° and 60°.

5. The pacing lead assembly of claim 1 wherein said flat planar device is in the shape of a wing with two wing portions each extending from one side of said passageway.

6. The pacing lead assembly of claim 5 wherein said locking means comprise a hub which has been fixed on the pacing lead and which has a radially extending rib thereon forming a key and said passageway has a larger diameter than the pacing lead and a diameter which is approximately the same as the diameter of said hub, one end of said passageway having a slot extending radially of said passageway and being shaped and configured to be received over and mate with said key when said slot is aligned with said key and said wing is moved over said hub into locking engagement therewith.

7. The pacing lead assembly of claim 6 wherein said passageway has a countersunk cavity in said one end and said hub has an end flange which is adapted to mate with and be received in said countersunk cavity.

8. The pacing lead assembly of claim 1 wherein said flat, planar device has indicia on each side thereof indicating which side should face flat against the skin of the patient and which side should face upwardly for receiving tape thereon.

9. The pacing lead assembly of claim 1 wherein said electrode assembly has a tip and said locking means are located approximately 30 cm from the tip of said electrode assembly.

10. The pacing lead assembly of claim 1 wherein said pacing lead has two depth indicating bands thereon, one indicating a 10 cm depth of penetration and the other indicating a 20 cm depth of penetration of the pacing lead.

11. The pacing lead assembly of claim 1 wherein said flat planar device is made of polyurethane.

* * * * *